United States Patent
Pocchiari et al.

[11] Patent Number: 6,107,318
[45] Date of Patent: Aug. 22, 2000

[54] NAPHTHOTHIAZOLONE DERIVATIVES ACTIVE ON THE $D_3$ DOPAMINERGIC RECEPTOR

[75] Inventors: Felice Pocchiari, Bresso; Claudio Masotto, Milan; Paolo Cavalleri, Saronno; Stefania Montanari; Francesco Santangelo, both of Milan, all of Italy

[73] Assignee: Zambon Group S.p.A., Vicenza, Italy

[21] Appl. No.: 09/424,858

[22] PCT Filed: Jun. 12, 1998

[86] PCT No.: PCT/EP98/03560

§ 371 Date: Dec. 6, 1999

§ 102(e) Date: Dec. 6, 1999

[87] PCT Pub. No.: WO98/56778

PCT Pub. Date: Dec. 17, 1998

[30] Foreign Application Priority Data

Jun. 13, 1997 [IT] Italy ................... MI97A1398

[51] Int. Cl.$^7$ .............. A61K 31/428; A61K 51/08; C07D 277/84

[52] U.S. Cl. .......... 514/366; 206/223; 206/569; 206/570; 424/1.65; 548/150

[58] Field of Search ............ 548/150; 514/366; 206/223, 569, 570; 424/1.65

[56] References Cited

U.S. PATENT DOCUMENTS 5,639,770  6/1997  Chihiro et al. .................. 514/365

FOREIGN PATENT DOCUMENTS

94/21608  9/1994  WIPO .

*Primary Examiner*—Laura L. Stockton
*Attorney, Agent, or Firm*—Arent Fox Kintner Plotkin Kahn

[57] ABSTRACT

A compound of Formula (I)

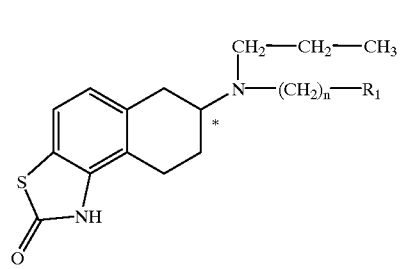

or a pharmaceutically acceptable salt thereof, wherein n is an integer between 2 and 6 and $R_1$ is a methyl group or a group

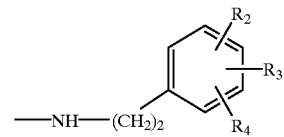

wherein $R_2$, $R_3$ and $R_4$ are independently hydrogen, hydroxy, methoxy, methylsulfonyl, or one of $R_2$, $R_3$ and $R_4$ together with another one of the three substituents forms a —O—$CH_2$—O— bridge. The asterisk marks an asymmetric carbon atom.

11 Claims, No Drawings

NAPHTHOTHIAZOLONE DERIVATIVES ACTIVE ON THE D₃ DOPAMINERGIC RECEPTOR

This application is a 371 of PCT/EP98/03560 filed Jun. 12, 1998.

The present invention relates to 4,5,6,7-tetrahydronaphthothiazolone derivatives selectively active on the $D_3$ dopaminergic receptor.

The $D_3$ dopaminergic receptor was cloned for the first time by Sokoloff et al. (Nature. 347. 146. 1990), and is abundant in the cerebral areas connected to the emotional and cognitive functions.

The patent application WO 96/23760 (in the name of Pharmacia & Upjohn) describes 2-aminoindanes with selective activity for the $D_3$ receptor.

The $D_3$-antagonists are said to have a potential use as antipsychotics. e.g. in the therapy of schizophrenia, schizoemotional diseases, psychotic depression, manias. The pathologies which may be treated with the $D_3$-receptor agonists include dyskinesia, such as Parkinson's disease, neuroleptic parkinsonism and late dyskinesia, and also depression, anxiety, memory failure, sexual disorders, drug addiction (e.g. from cocaine).

The patent application EP 0 186 087 (in the name of Karl Thomae GmbH) discloses tetrahydrobenzothiazoies N-substituted on both the rings useful as $D_2$ and $D_3$ receptor agonists, and thus useful in the treatment of schizophrenia and Parkinson's disease One of these compounds, 2-amino-6-n-propylamino-4,5,6,7-tetrahydrobenzothiazole, is further claimed in the patent application WO 96/18395 (in the name of Up-john/Boehringer Ingelheim) as endowed with neuroprotective effect.

We have now found a new class of compounds endowed with selective activity on the $D_3$ doparninergic receptors as antagonists, agonists or partial agonists.

Therefore the present invention relates to compounds of formula I

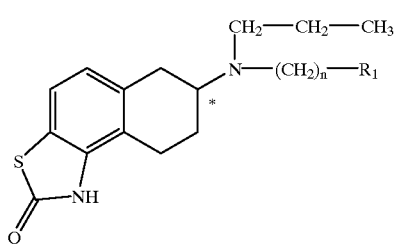

(I)

wherein n is an integer comprised between 2 and 6.
$R_1$ is a methyl group or a group

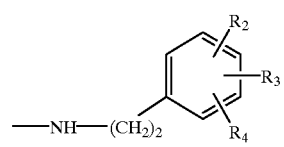

wherein $R_2$, $R_3$ and $R_4$ are independently hydrogen, hydroxy, methoxy, methylsulfonyl, or one of $R_2$, $R_3$ and $R_4$ together with another one of the three substituents forms a —O—CH₂—O— bridge;
the asterisk marks an asymmetric carbon atom;
and the pharmaceutically acceptable salts thereof.

The compounds of formula I have at least an asymmetric centre, marked by an asterisk, and may therefore be in form of stereoisomers.

Object of the present inventions are the compounds of formula I in form of stereoisomeric mixture and also as single stereoisomers.

The compounds of formula I are active on the $D_3$ dopamineraic receptors also by oral route. They are therapeutically useful in the treatment of psychotic diseases, such as schizophrenia, dyskinesia, such as Parkinson's disease, of depression, anxiety, memory diseases, sexual disorders and drug addiction.

Preferred compounds of formula I are the ones wherein the carbon atom marked by an asterisk has the S configuration.

Pharmaceutically acceptable salts of the compounds of formula I are salts with organic and inorganic acids such as, e.g., hydrochloric, hydrobromic, hydroiodic, nitric, sulphuric, phosphoric, acetic, benzoic, maleic, fumaric, succinic, citric, aspartic, methansulfonic and 3,7-di-t.butylnaphthalen-1,5-disulfonic (dibudinic acid).

The preparation of the compounds of formula I is effected according to methods known by the skilled in the art. For example, a compound formula II

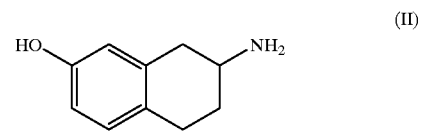

(II)

or a salt thereof is duly protected on the amino group, for example with diterbutylcarbonate, phthalic anhydride or trifluoroacetic anhydride; the hydroxy group is then turned into a polyfluoroalkylsultonyioxy group ($R_fSO_2O$—) such as, for example, trifluoromethylsulfonyloxy, thereby yielding a compound of formula III

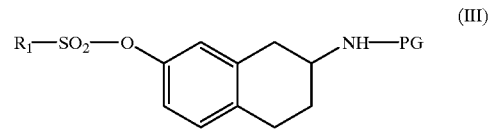

(III)

wherein $R_f$ is a lower polyfluoroalkiyl group and PG a protecting group, which is nitrated for example with nitric acid or other nitrating agzents such as ammonium nitrate/trifluoroacetic anhydride or nitroniurn tetrafluoroborane, to give a compound of formula IV

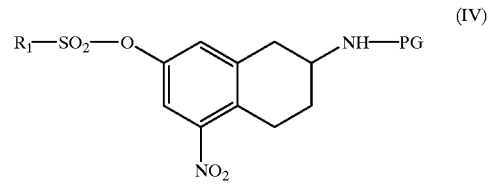

(IV)

wherein $R_f$ and PG are as defined above. The nitro group of the compound of formula IV is reduced to amino by hydrogenation in the presence of a catalyst made of a metal such as palladium, platinum, nickel, rhodium and ruthenium; in the meantime the polfluoroalkylsulfonyioxy group is reduced, thus obtaining a compound of formula V

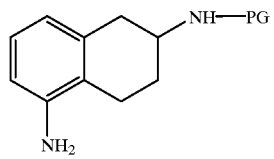
(V)

wherein PG is as defined above, which is reacted with a thiocyanate such as, for example, ammonium or alkali metal thiocyanate, in acidic environment to give a compound of formula VI

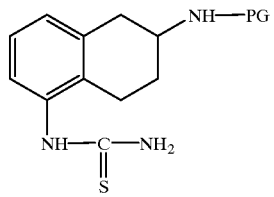
(VI)

wherein PG is as defined above. This compound is cyclized to an aminothiazole derivative by heating in the presence of thionyl chloride or bromine in chloroform, and then turned in the equivalent diazonium salt applying known techniques. The diazonium salt is turned in the compound of formula VII

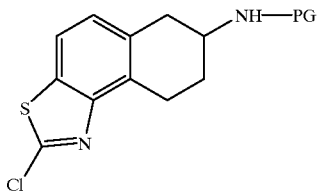
(VII)

wherein PG is as defined above, by treatment with copper (I)chloride. Alternatively, the compound of formula VII may be directly obtained from the aminothiazole compound by treatment with copper(II)chloride and t-butylnitrite. The compound of formula VII is reacted with sodium methylate and then the amino group is deprotected to give a compound of formula VIII

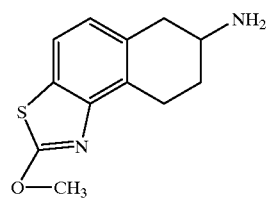
(VIII)

which is reacted with propionic aldehyde in the presence of sodium cyanoborohydride or under other conditions for reductive ammination.

The compound of formula IX is reacted under dehydrating conditions with an acid of formula X

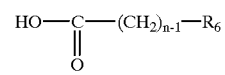
(X)

wherein n is as defined above and $R_6$ is hydrogen or a group

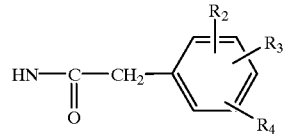

wherein $R_2$, $R_3$ and $R_4$ are as defined above, or with a reactive derivative thereof such as an acyl halide or a mixed anhydride which may also be prepared in situ in an inert solvent in the presence of a base such as an alkali carbonate or bicarbonate or a tertiary amine, to give an intermediate of formula XI

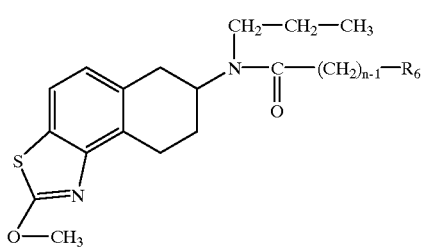
(XI)

wherein n and $R_6$ are as defined above, which is treated with hydrochloric acid in hot tetrahydrofiran and subsequently reduced on all the present amido groups by a reducing agrent such borane or borane complexes, for example, with methylsulfide or lithium aluminium hydride, to give the compounds of formula I.

A specific alternative relates to the compounds of formula I wherein n is 2 and $R_1$ is methyl which may be prepared by reacting the compound offormula VIII above with a double amount of propionic aldehyde under the just mentioned conditions.

A compound of formula IX is thus obtained

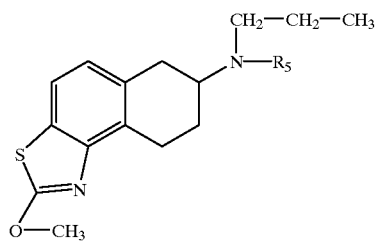
(IX)

wherein $R_5$ is hydrogen or a propyl group. The treatment of the compound of formula IX wherein $R_5$ is propyl with hydrochloric acid in dioxane and methanol allows the obtainment of the compounds of formula I wherein $R_1$ is methyl and n=2.

The compounds of formula I in optically active form are obtained by optical separation or through stereospecific or stereoselective synthesis.

The preparation of the salts of the compounds of formula I is carried out according to conventional methods.

The compounds of formula I are active on the $D_3$ dopaminergic receptors. The interaction test with other receptorial systems showed that the compounds of formula I do not notably interact and thus they are endowed with high specificity (Example 12).

It is apparent that these selectivity and specificity features make the compounds of formula I particularly suitable for the treatment of central diseases and in the antipsychotic therapy, in that of the dyskinesia, in the treatment of depression, anxiety, memory problems, sexual disorders and drug addiction.

Moreover these compounds may be used as selective markers for the $D_3$ receptors optionally in form of radioligands.

As a consequence in the therapeutical practice the compounds of formula I may be administered both parenterally and enterally. The therapeutical doses usually range between 0.1 mg and 400 mg a day by oral route for single administration.

Another object of the present invention are the pharmaceutical compositions containing a therapeutically effective amount of the compounds of formula I or the pharmaceutically acceptable salts thereof in admixture with a suitable carrier.

The pharmaceutical compositions of the invention may be liquid, suitable to the enteral or parenteral administration, and, preferably, solid such as tablets, capsules, granulates, suitable to the oral administration.

The preparation of the pharmaceutical compositions of the invention may be carried out according to common techniques.

A further object of the invention relates to diagnostic kit containing one of the compounds of formula I optionally in form of radioligand.

For better illustrating the present invention the following examples are now provided.

The chromatographic purifications were effected on silica gel columns (230–400 mesh). Unless otherwise specified, the mass spectra were effected under the following conditions: chemical ionisation, isobutane, positive ions.

EXAMPLE 1

Synthesis of (S)-7-trifluoroacetylamino-5,6,7,8-tetrahydro-2-naphthyl trifluoromethansulfonate A suspension of 7-hydroxy-1,2,3,4-tetrahydro-2-naphtylamine hydrobromide (12.2 g; 50 mmoles) (prepared as described in the patent application FR 2653765 in the name of Midy) and triethylamine (25 ml; 175 mmoles) in $CH_2Cl_2$ (400 ml) and acetonitrile (20 ml), under stirring at room temperature, was dropwise added with a solution of trifluoroacetic anhydride (8.3 ml; 57.5 mmoles) in $CH_2Cl_2$ (100 ml). After 2 hours water was added (200 ml). The organic phase was washed first with a 1N solution of HCl (200 ml) then with water (200 ml), anhydrified over $Na_2SO_4$ and the solvent evaporated under reduced pressure. The crude was dissolved in acetonitrile (300 ml) The resulting solution wvas added with $K_2CO_3$ (12.5 g; 90.7 mmoles) and, dropwise, with a solution of N-phenyltrifluoromethansulfonimide (17 g; 47.6 mmoles) in acetonitrile (100 ml) at room temperature. The mixture was stirred at room temperature for 18 hours, then the solvent was evaporated under reduced pressure. The residue was added with ethyl ether (600 ml) and water (300 ml). The phases were separated and the organic one washed first with a 1N solution of HCl (300 ml) then with water (300 ml), anhydrified over $Na_2SO_4$, and the solvent evaporated under reduced pressure. The crude was purified by silica gel chromatography (eluent petrolatum:ethyl acetate=8:2).

There were obtained 16.1 g of (S)-7-triluoroacetylamino-5,6,7,8-tetrahydro-2-naphthyl trifluoromethansulfonate.

$^1$H-NMR (200 Mhz, $CDCl_3$): δ (ppm) 1.75–1.97 (m, 1H); 2.07–2.22 (m, 1H); 2.76 (dd, 1); 2.87–2.98 (m, 2H); 3.20 (dd, 1H); 4.20–4.40 (m, 1H); 6.33 (bd, 1H); 6.97 (d, 1H); 7.05 (dd, 1H); 7.18 (d, 1H).

Mass: 392 $(M+H)^+$.

EXAMPLE 2

Synthesis of (S)4-nitro-7-trifluoroacetylamino-5,6,7,8-tetrahydro-2-naphthyl trifluoromethansulfonate A solution of (S)-7-trifluoroacetyiamino-5,6,7,8-tetrahydro-2-naphthyl trifluoromethansulfonate (15.8 g; 40.4 mmoles), prepared as described in example 1, in trifluoroacetic acid (150 ml), under stirring at 0° C., was dropwise added with 100% $HNO_3$ (2.1 ml; 52.5 mmoles). At the end of the addition the mixture was left to rise to room temperature and after 50 minutes poured into water and ice (1200 ml). The formed precipitate was filtered the dissolved in ethyl ether (600 ml). The organic phase was washed with water (2×300 ml), anhrdrified over anhydrous $Na_2SO_4$ and the solvent evaporated under reduced pressure. The resulting crude was purified by silica gel chromatography (eluent petrolatum:ethyl acetate=8:2).

There were obtained 9.8 g of (S)-4-nitro-7-trifluoroacerylamino-5,6,7,8-tetrahydro-2-naphthyl trifluoromethansulfonate.

$^1$H-NMR (200 MHz, $CDCl_3$): (ppm) 1.74–1.97(m,1H); 2.15–2.31(m,1H); 2.89(dd,1H); 3.12–3.24(m,2H); 3.38(dd, 1H); 4.21–4.41(m,1H); 6.38(bd,1H); 7.28(d,1H); 7.72(d, 1H).

Mass: 437 $(M+H)^+$.

EXAMPLE 3

Synthesis of (S)-N-(5-amino-1,2,3,4-tetrahydro-2-napthyl)trifluoroacetamide

A mixture of (S)-4-nitro-7-trifluoroacetylamino-5,6,7,8-tetrahydro-2-naphthyl trifluoromethansulfonate (9.8 g; 22.5 mmoles), prepared as described in example 2, and triethylamine (8.2 ml; 56.2 mmoles) in methanol (500 ml) was kept under hydrogen pressure (50 psi=3.4 atm) in the presence of 10% Pd/C (5 g) for 1.5 hour at room temperature. After filtering off the catalyst the mixture was concentrated to dryness under reduced pressure. The residue was dissolved in ethyl acetate (300 ml) and the solution washed with water (3×200 ml), anhydrified over anhydrous $Na_2SO_4$ and the solvent evaporated under reduced pressure. The crude was purified by silica gel chromatography (eluent methylene chloride:methanol=98.2).

There were obtained 4.4 g of (S)-N-(5-amino-1,2,3,4-tetrahydro-2-naphtyl)-trifluoroacetamide.

$^1$H-NMR (200 MHz, $CDCl_3$): δ (ppm) 1.83–2.24(m,2H); 2.58(m,2H); 2.71(dd,1H); 3.12(dd,1H); 3.60(bs,2H); 4.22–4.41(m,1H); 6.26(bd,1H); 6.55(m,2H); 6.99(m,1H).

Mass (electronic impact): 258 $(M+H)^-$.

The product was subsequently turned into the corresponding hydrochloride by dissolution into ethyl acetate saturated with HCl followed by evaporation of the solvent under reduced pressure.

EXAMPLE 4

Synthesis of (S)-6-trifluoroacetylamino-5,6,7,8-tetrahydro-1-naphthylthiourea

A suspension of (S)-1,2,3,4-tetrahydro-1,5-naphthalendiamine-2-trifluoroacetamide hydrochloride (4.4 g; 14.9 mmoles), prepared as described in example 3, in chlorobenzene (45 ml), under stirring at 50° C., was added with 12N HCl (0.13 ml) and ammonium thiocyanate (2.27 g; 29.9 mmoles). The mixture was heated to 115° C. for 3 hours. After evaporating the solvent under reduced pressure the resulting residue was added with ethyl acetate (200 ml) and water (100 ml). The organic phase was washed with water (100 ml), anhydrified over anhydrous $Na_2SO_4$ and concentrated to dryness under reduced pressure. The resulting crude was purified by silica gel chromatography (eluent methylene chloride:methanol=95:5).

There were obtained 3 g of (S)-6-trifluoroacetyiamino-5,6,7,8-tetrahydro-1-naphthylthiourea.

$^1$H-NMR (200 MHz, DMSO-$d_6$): δ (ppm) 1.59–2.08 (m, 2H); 2.61–3.08 (m, 4H); 3.91–4.13 (m, 1H); 6.98–7.19 (m, 3H); 9.16 (bs, 1H); 9.49 (bd, 1H).

Mass (thermospray): 318 (M+H)$^-$.

EXAMPLE 5

Synthesis of (S)-2-chloro-6-trifluoroacetylamino-4,5,6,7-tetrahydronaphtho(1,2-d)thiazole A solution or (S)-6-trifluoroacetylamino-5,6,7,8-tetrahydro-1-naphthylthiourea (2.6 g; 8.2 mmoles), prepared as described in example 4, in thionyl chloride (4 ml) was heated to 60° C. for 1.5 hour. After cooling to 0° C. water was added (50 ml) and the mixture heated again to 80° C. for 2 hours, then brought to room temperature, alkalinised with 30% ammonia and extracted with ethyl acetate. The organic phase was washed with water, anhydrified over anhydrous $Na_2SO_4$ and concentrated to dryness under reduced pressure. The residue was dissolved in ethyl acetate. After adding ethyl acetate saturated with HCl a precipitate was obtained, filtered on a porous sect and washed with petrolatum on the filter. The resulting solid, dried under vacuum at 50° C. overnight, was portionwise added to a suspension of copper(II)chloride (1 g; 7.4 mmoles) and t-butylnitrite (1.1 ml; 9.2 mmoles) in dry acetonitrile (50 ml), under stirring at 60° C. After 25 minutes the reaction mixture was brought to room temperature and poured into 20% HCl. After extraction with ethyl ether the organic phase was washed first with 2N HCl then with water, anhydrified over anhydrous $Na_2SO_4$ and concentrated to dryness under reduced pressure, The resulting crude was purified by silica gel chromatography (eluent petrolatum:ethyl acetate=8:2).

There were obtained 1.4 g of (S)-2-chloro-6-trifluoroacetyiamino-4,5,6,7-tetrahydronaphtho(1,2-d)thiazole.

$^1$H-NMR (200 MHz, CDCl$_3$): δ (ppm) 1.84–2.07(m, 1H); 2.14–2.31(m, 1H); 2.83(dd, 1H); 3.13–3.49(m, 3H); 4.20–4.39 (m, 1H); 6.2 (bd, 1H); 7.12 (d, 1H); 7.55 (d, 1H).

Mass (thermospray): 335 (M+H)$^-$.

EXAMPLE 6

Synthesis of (S)-2-methoxy-6-amino-4,5,6,7-tetrahydronaphtho(1,2-d)thiazole

Sodium (0.22 g; 9.6 mmoles) was portionwise added to dry CH$_3$OH (30 ml), under stirring at room temperature. When the dissolution was completed a portion of (S)-2-chloro-6-trifluoroacetylamino-4,5,6,7-tetrahydronaphtho(1,2-d)thiazole (1.4 g; 4.2 mmoles), prepared as described in example 5, was added and the mixture refluxed for 5 hours. After cooling to room temperature water (2 ml) and a 32% solution of NaOH (0.5 ml) were added and the mixture was refluxed again for 2 hours. After evaporation of the solvent under reduced pressure the residue was added with methylene chloride and water. The phases were separated and the organic one was washed with a saturated solution of NaCl, anhydrified over anhydrous $Na_2SO_4$ and concentrated to dryness under reduced pressure.

There was obtained 0.95 g of (S)-2-methoxy-6-amino-4,5,6,7-tetrahydronaphtho(1,2-d)thiazoie.

$^1$H-NMR (200 MHz, CDCl$_3$): δ (ppm) 1.43 (bs, 2H); 1.51–1.74 (m, 1H); 2–2.17 (m, 1H); 2.6 (m, 1H); 2.89–3.4 (m, 4H); 4.16 (s. 3H); 6.93 (d, 1H); 7.38 (d, 1H).

Mass (thermospray): 235 (M+H)$^-$.

EXAMPLE 7

Synthesis of (S)-2-methoxy-6-dipropylamino-4,5,6,7-tetrahydronaphtho(1,2-d)-thiazole A solution of (S)-2-methoxy-6-amino-4,5,6,7-tetrahydronaphtho(1,2-d)thiazole (0.1 g; 0.42 mmoles), prepared as described in example 6, in CH$_3$OH (5 ml), under stirring at room temperature on 3Å molecular sieves, was added with sodium acetate (56 mg; 0.68 mmoles), sodium cyanoborohydride (54 mg; 0.85 mmoles) and propionic aldehyde (0.09 ml; 1.26 mmoles). After 18 hours the reaction mixture was poured into water. After extraction with ethyl acetate the organic phase was washed with a saturated solution of NaCl, anhydrified over $Na_2SO_4$ and concentrated to dryness under reduced pressure. The resulting crude was purified by silica gel chromatography (eluent methylene chloride:methanol; 30% ammonia=90:10:0.5).

There were obtained 108 mg of (S)-2-methoxy-6-dipropylamino-4,5,6,7-tetrahydronaphtho(1,2-d)thiazole.

$^1$H-NMR (200 MHz, CDCl$_3$): δ (ppm) 0.89(t,6H); 1.37–1.75(m,5H); 2.03–2.18(m,1H); 2.49(m,4H); 2.71–3.09 (m,4H); 3.40(m,1H); 4.16(s,3H); 6.95(d,1H); 7.37(d,1H).

Mass (thermospray): 319 (M+H)$^-$.

EXAMPLE 8

Synthesis of (S)-6-dipropylamino-4,5,6,7-tetrahydronaphtho(1,2-d)thiazol-2(3H)-one hydrochloride (Compound 1)

A solution of (S)-2-methoxy-6-dipropylamino-4,5,6,7-tetrahydronaphtho(1,2-d)-thiazole (0.1 g; 0.31 mmoles), prepared as described in example 7, in methanol (1 ml) and dioxane (3 ml) was added with 3 drops of 37% HCl. The mixture was stirred at room temperature for 6 hours, then the solvents were evaporated under reduced pressure. There were obtained 107 mg of (S)-6-dipropylamino-4,5,6,7-tetrahydronaphtho(1,2-d)thiazol-2(3H)-one hydrochloride.

$^1$H-NMR (200 MHz, D$_2$O): δ (ppm) 0.84 (t. 6H); 1.50–2.23 (m, 6H); 2.47–3.14 (m, 8H); 3.49–3.66 (m, 1H); 6.81 (d, 1H); 7.10 (d, 1H).

Mass (thermospray): 305 (M+H)$^-$.

EXAMPLE 9

Synthesis of (S)-2-methoxy-6-propylamino-4,5,6,7-tetrahydronaphtho(1,2-d)thiazole A solution of (S)-2-methoxy-6-amino-4,5,6,7-tetrahydronaphtho(1,2-d)thiazole (0.35 g; 1.49 mmoles), prepared as described in example 6, in methanol (15 ml), under stirring at room temperature on 3 Å molecular sieves, was added with sodium acetate (196 mg; 2.4 mmoles), sodium cyanoborohydride (188 mg; 3 mmoles) and propionic aldehyde (0.107 ml; 1.49 mmoles). After 25 hours the mixture was evaporated to dryness under reduced pressure and the resulting residue was added with ethyl acetate and water. The phases were separated and the organic one was washed with a saturated solution of NaCl, anhydrified over anhydrous $Na_2SO_4$ and concentrated to dryness under reduced pressure. The resulting crude was purified by silica gel chromatography (eluent methylene chloride:methanol:30% ammonia=90:10:0.5).

There were obtained 270 mg of (S)-2-methoxy-6-propylamino-4,5,6,7-tetrahydronaphtho(1,2-d)thiazole.

$^1$H-NMR (200 MHz, $CDCl_3$): δ (ppm) 0.93 (t, 3H); 1.43–2.21 (m, 5H); 2.57–3.14 (m, 6H); 3.30 (m, 1H); 4.16 (s, 3H); 6.95 (d, 1H); 7.37 (d, 1H).

Mass (thermospray): 277 $(M+H)^-$.

EXAMPLE 10

Synthesis of (S)-6-N-propyl-N-6-[(4-methylsulfonylohenyl)acetylamino]-1-keto-hexyl-amino-4,5,6,7-tetrahydronaphtho(1,2-d)thiazol-2(3H)-one A suspension of 6-(4-methylsulfonylphenyl) acetamidohexanoic acid (320 mg, 0.95 mmoles) in methylene chloride (5 ml) was added under stirring at room temperature with thionyl chloride (0.082 ml; 1.13 mmoles). After 1.5 hour the solvent and the exceeding thionyl chloride were evaporated under reduced pressure. The resulting oil was dissolved in methylene chloride (5 ml) and the obtained solution was dropwise added, under stirring at room temperature, to a solution of (S)-2-methoxy-6-propylamino-4,5,6,7-tetraihydronaphtho(1,2-d)thiazole (240 mg; 0.87 mmoles), prepared as described in example 9, and triethylamine (0.38 ml; 2.6 mmoles) in methylene chloride (20 ml). After 1 hour the reaction mixture was poured into water and methylene chloride. The organic phase was washed first with a 5% solution of $KHCO_3$ then with water, anhydrified over anhydrous $Na_2SO_4$ and concentrated to dryness under reduced pressure, the residue was dissolved in THF (15 ml) and the solution was added with 3 drops of 37% HCl. The reaction mixture was heated to 60° C. for 6 hours, then evaporated to dryness under reduced pressure and the resulting residue was added with methylene chloride and water. The phases were separated and the organic one was washed with water, anhydrified over anhydrous $Na_2SO_4$ and concentrated to dryness under reduced pressure. The obtained crude was purified by silica gel chromatography (eluent methylene chloride:methanol=9:1).

There were obtained 450 mg of (S)-6-N-propyl-N-6-[(4-methylsulfonylphenyl)acetyl-amino]-1-keto-hexyl-amino-4,5,6,7-tetrahydronaphtho(1,2-d)thiazol-2(3H)-one.

$^1$H-NMR (200 MHz, $CDCl_3$): δ (ppm) 0.90 and 0.93 (2t, 3H); 1.22–2.18 (m, 10H); 2.29–2.41 (m, 2H); 2.72–3.36 (m, 8H); 3.02 and 3.04 (2s, 3H); 3.60 (s, 2H); 3.89–4.11 and 4.47–4.69 (2m, 1H); 6.25 and 6.39 (2bt, 1H); 6.79–6.93 (2d, 1H); 7.09–7.23 (2d, 1H); 7.43–7.90 (m, 4H); 9.83 and 9.90 (2bs, 1H).

Mass (thermospray): 572 $(M+H)^-$.

EXAMPLE 11

Synthesis of (S)-6-N-propyl-N-6-[2-(4-methylsulfonylphenyl)ethylamino]hexylamino-4,5,6,7-tetrahydronaphtho(1,2-d)thiazol-2(3H)-one dihydrochloride (Compound 2)

A solution of (S)-6-N-propyl-N-6-[(4-methylsulfonylphenyl)acetylamino]-1-keto-hexyl-amino-4, 5,6,7-tetrahydronaphtho(1,2-d)thiazol-2(3H)-one (300 mg; 0.52 mmoles), prepared as described in example 10, in dry THF (15 ml) was dropwise added with borane methylsulfide (0.4 ml; 4.2 mmoles) under stirring at room temperature. At the end of the addition the mixture was refluxed for 3 hours. After cooling to 5° C. a solution of 37% HCl (0.4 ml) in methanol (4 ml) was dropwise added, the mixture was refluxed again for 3 hours. The crude obtained after evaporation of the solvents under reduced pressure was purified by silica gel chromatography (eluent methylene chloride:methanol:50% formic acid=85:15:2). The resulting product was dissolved in absolute ethanol and this solution was brought to neatly acid pH by adding ethyl ether saturated with HCl. After evaporation under reduced pressure there were obtained 210 mg of (S)-6-N-propyl-N-6-(2-(4-methylsulfonylphenyl)-ethyl-amino)hexyl-amino-4,5,6,7-tetrahydronaphtho-(1,2-d)-thiazol-2(3H)-one dihydrochloride.

$^1$H-NMR (200 MHz, $D_2O$): δ (ppm) 0.84 (t, 3H); 1.23–2.26 (m, 12H); 3.07 (s, 3H); 2.51–3.23 (m, 14H); 3.56–3.72 (m, 1H); 6.83–7.13 (m, 2H); 7.36–7.74 (m, 4H).

Mass (thermospray): 544 $(M+H)^-$.

EXAMPLE 12

Test for evaluating the bindings to dopaminergic receptors in cell cultures

Chinese hamster ovary cells (CHO) transfected with dopaminergic receptor subtypes and murine mesencephalic neuronal (NM9D) expressing the different subtypes of such receptors were used. The cell lines were grown on Petri dishes, in a mixture of DMEM and Ham's F12 medium 1:1 supplemented with 10% foetal bovine serum (FBS), penicillin, streptomycin, geneticin (500 µg/ml) and glutamin in a humidified 5% $CO_2$ atmosphere at 37° C. When cells reached confluence they were washed with 10 ml of PBS (KCl 2.68 mM, $KH_2PO_4$ 1.4 mM, NaCl 0.13 mM and $Na_2HPO_4$ 6.4 mM) then 5 ml of lysis buffer (Tris-HCl 10 mM and EDTA 5 mM) were added to each Petri. Cells were scrapped and the solution centrifuged for 20 minutes at 48,000 gravity, 4° C. The pellet was suspended in a minimal amount of lysis buffer and homogenised for 15 seconds. The membrane solution was aliquotated in portions of from 1 to 1.5 ml at a protein concentration of about 3 mg/ml (measures by a Bio-Rad protein assay based on the differential change of colour of a dye in response to different concentration of protein), placed in plastic tubes, rapidly frozen in liquid nitrogen and stored at −80° C. The binding test was performed as reported by Billard et al. 1984, Life Sciences, 35. 1885–1893. Seabrook et al. 1992, FEBS, 312, 123–126 and Sunahara et al. 1991, Nature, 350, 614–619. For saturation experiments [3H]-SCH23390 (Amersharm; specific activity=70 Curie/mmole) was used as radioligand for $D_1$ receptors, $D_5$ and [3H]-spiperone (Amersharm; specific activity=113 Curie/mmole) for $D_2$, $D_3$ and $D_4$ receptors. Saturation curves were analysed using Ligand® program to have Kd (dissociation constant) and Bmax (number of receptors/mg of protein) (Munson and Rodbar, 1980Anal. Biochem., 107, 220–239).

Displacement studies were performed on cell membrane at the following conditions:

| Receptor | Radioligand | Radioligand Concentration | Non specific |
|---|---|---|---|
| $D_1$ | [3H]-SCH23390 | 0.2 nM | (−)cis-flupenthixol (1 μM) |
| $D_5$ | [3H]-SCH23390 | 0.2 nM | (−)cis-flupenthixol (1 μM) |
| $D_{2s}$ | [3H]-spiperone | 0.1 nM | (+)-butaclamol (1 μM) |
| $D_3$ | [3H]-spiperone | 0.3 nM | (+)-butaclamol (1 μM) |
| $D_4$ | [3H]-spiperone | 0.2 nM | (+)-butaclamol (1 μM) |

The compounds of the invention were tested at increasing concentrations for evaluating their binding to the various receptors, expressed as Ki (affinity constant) obtained through the Cheng and Prusoff equation The results are shown in Table 1.

TABLE 1

| | Receptor binding (Ki nM) | | | | |
|---|---|---|---|---|---|
| Compound | $D_1$ | $D_5$ | $D_{2s}$ | $D_3$ | $D_4$ |
| 1 | >$10^4$ | >$10^4$ | n.d. | 489 | 9841 |
| 2 | >$10^4$ | 9273 | 9440 | 92 | >$10^4$ |

The compounds of formula I show to selectively bind $D_3$ receptor having an affinity constant for the remaining tested receptors neatly higher.

What is claimed is:

1. A compound of formula

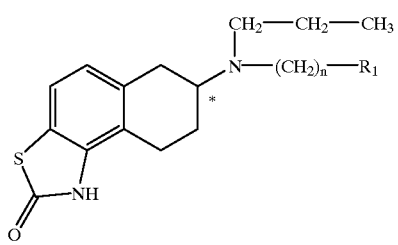

(I)

wherein n is an integer between 2 and 6;

$R_1$ is a methyl group or a group

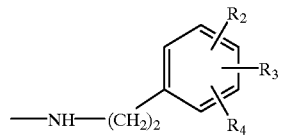

wherein $R_2$, $R_3$ and $R_4$ are independently hydrogen, hydroxy, methoxy, methylsulfonyl, or one of $R_2$, $R_3$ and $R_4$ together with another one of the three substituents forms a —O—$CH_2$—O— bridge;

the asterisk marks an asymmetric carbon atom;

or a pharmaceutically acceptable salt thereof.

2. A compound according to claim 1 wherein the carbon atom marked by an asterisk has the S configuration.

3. A compound according to claim 1 in optically active form.

4. A process for preparing a compound according to claim 1 comprising the reduction and the subsequent treatment with hydrochloric acid of a compound of formula

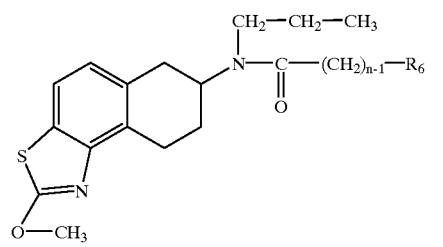

(XI)

wherein $R_6$ is hydrogen or a group

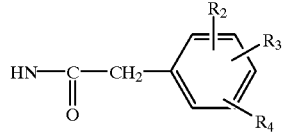

and n, $R_2$, $R_3$ and $R_4$ are as defined in claim 1.

5. A pharmaceutical composition containing a therapeutically effective amount of a compound according to claim 1 in admixture with a suitable carrier.

6. A pharmaceutical composition according to claim 5 for the treatment of psychotic disease, of dyskinesia, of depression, anxiety, memory problems, sexual disorders and drug addiction.

7. A diagnostic kit containing a compound according to claim 1.

8. A diagnostic kit containing a compound according to claim 1 in the form of a radioligand.

9. A method of treating a disorder associated with a $D_3$ receptor in a patient in need thereof, the method comprising administering to the patient a disorder treating effective amount of a compound according to claim 1.

10. A method of selectively binding a $D_3$ receptor, the method comprising providing an in vitro cell sample having $D_3$ receptors; and adding a compound according to claim 1 to the sample to selectively bind the $D_3$ receptors.

11. The method according to claim 10 wherein the compound is in the form of a radioligand.

* * * * *